United States Patent
Doty

(10) Patent No.: US 6,557,394 B2
(45) Date of Patent: May 6, 2003

(54) SMELL TEST DEVICE

(76) Inventor: Richard L. Doty, 125 White Horse Pike, Haddon Heights, NJ (US) 08035

( * ) Notice: Subject to any disclaimer, the term of this patent is extended or adjusted under 35 U.S.C. 154(b) by 0 days.

(21) Appl. No.: 09/822,607

(22) Filed: Apr. 2, 2001

(65) Prior Publication Data

US 2002/0139170 A1 Oct. 3, 2002

(51) Int. Cl.⁷ .............. G01N 7/00; G09B 25/00
(52) U.S. Cl. ............ 73/23.34; 442/96; 434/404; 116/298; 116/318
(58) Field of Search .............. 600/303; 73/23.34; 442/96; 428/905; 128/630, 920; 434/404; 116/114, 298, 318

(56) References Cited

U.S. PATENT DOCUMENTS 3,249,085 A * 5/1966 St. Jean ............ 116/304
4,687,203 A * 8/1987 Spector ............ 273/157 R

FOREIGN PATENT DOCUMENTS

| DE | 3313614 A1 | * | 10/1984 |
| FR | 2200998 | * | 4/1974 |
| FR | 2616675 A1 | * | 6/1987 |
| FR | 2777997 A1 | * | 4/1999 |

OTHER PUBLICATIONS

WO 89/00398, Cotman, Carl W. et al., Jan. 26, 1989.*
Doty et al., 1981 (no month), Proc. XIIth ORL World Congr., pp. 5–8.*
Richard L. Doty, Smell Identification Test, 1988.

* cited by examiner

Primary Examiner—Hezron Williams
Assistant Examiner—Michael Cygan
(74) Attorney, Agent, or Firm—Norman E. Lehrer

(57) ABSTRACT

The test includes a test panel placed between and rotatably secured to a cover and a rear panel. The cover has two windows located adjacent each other. Located adjacent the periphery of the test panel are twelve labels. Below each label is a set of choices. When the cover is placed over the test panel and secured thereto the first set of choices and label should be aligned with their respective windows. To use the test, the person scratches the label located above the first set of choices and then immediately sniffs the label. The person then chooses the item which most closely corresponds with what he/she smells and marks it by darkening the circle located adjacent his/her choice. Once all of the labels have been smelled and the choices marked, the test panel is rotated once more. The correctly marked choices will appear in openings formed on the cover.

4 Claims, 2 Drawing Sheets

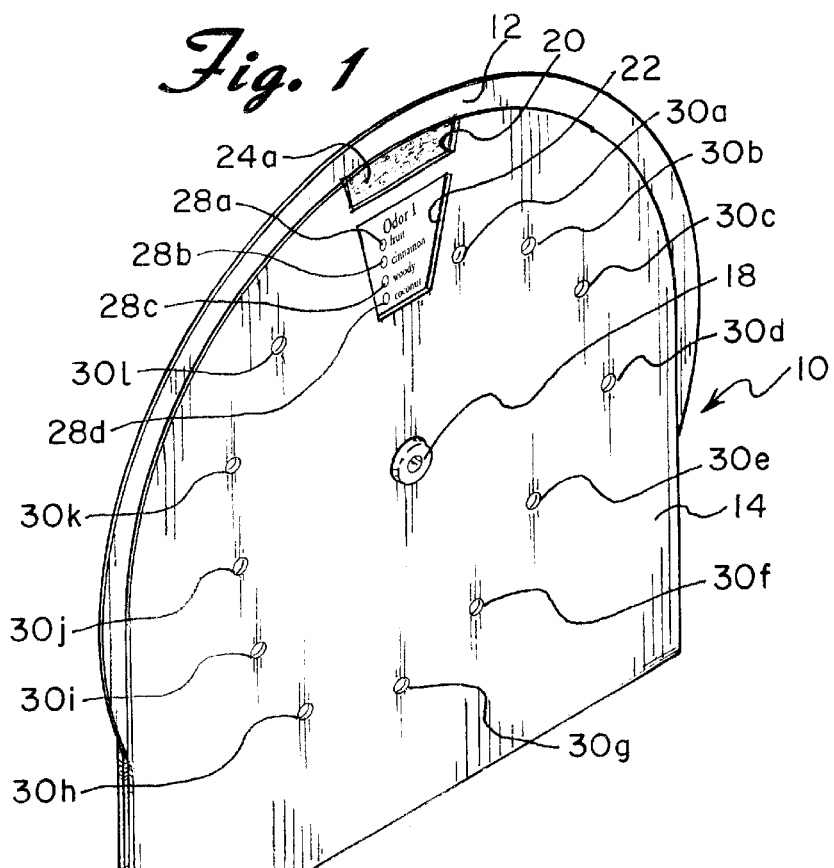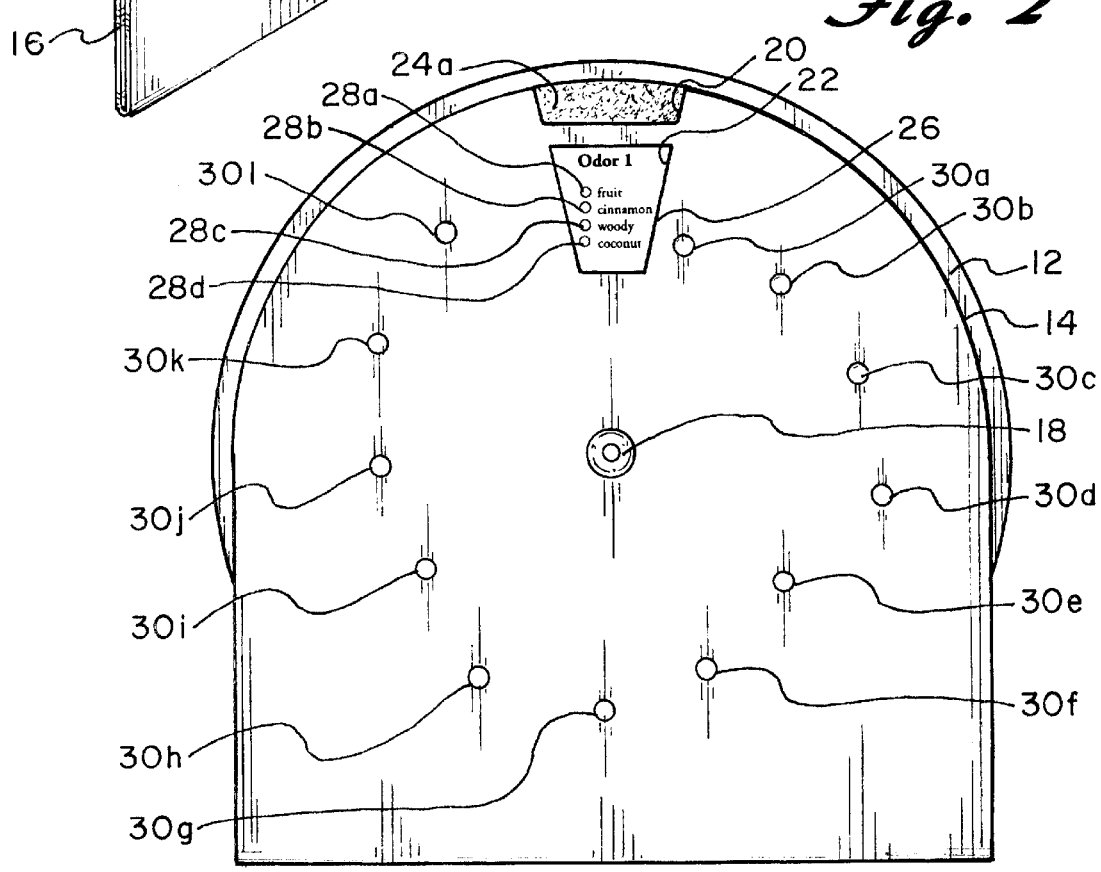

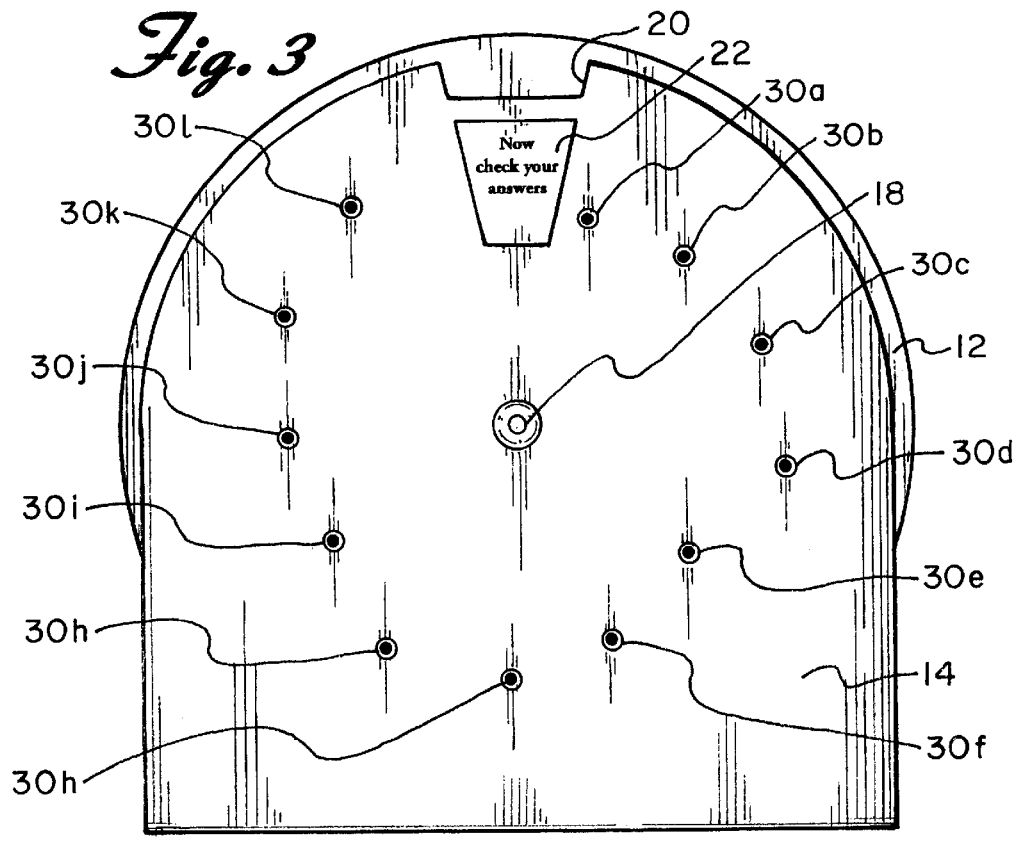
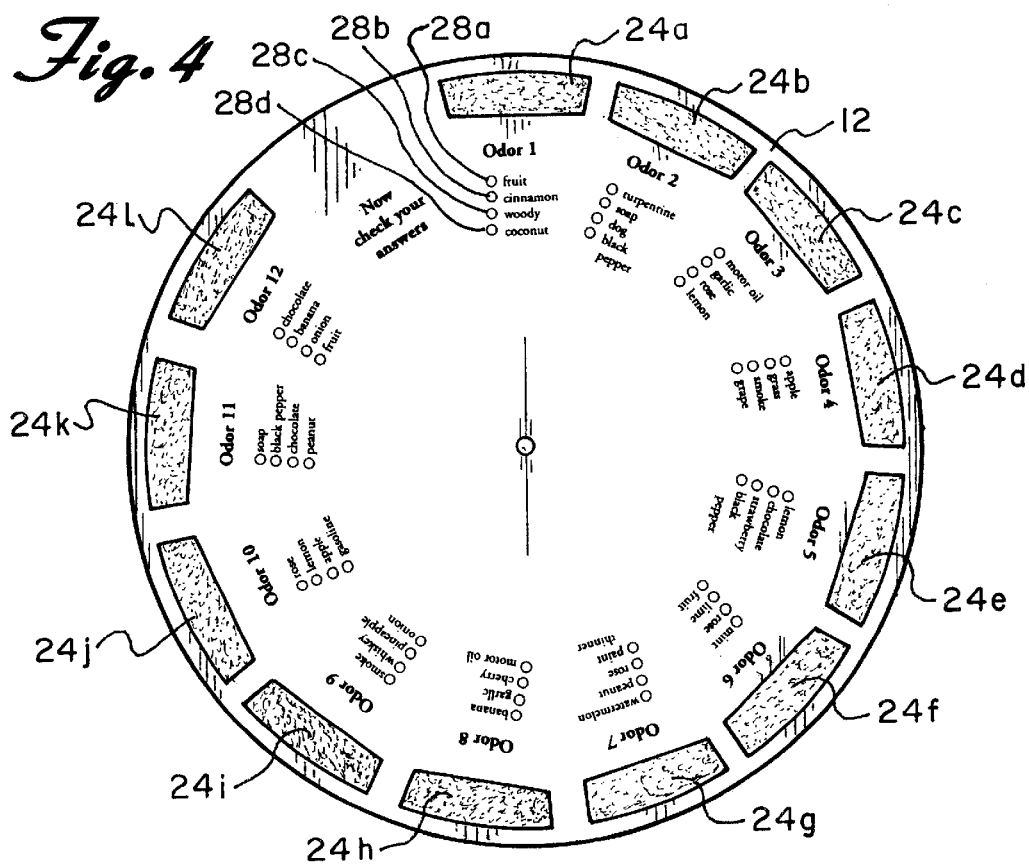

SMELL TEST DEVICE

BACKGROUND OF THE INVENTION

The present invention is directed toward a test for assessing a person's sense of smell and more particularly, toward a test which is easy to use and can be evaluated by the individual taking the test.

It is well known to otorhinolaryngologists and many other physicians that olfactory disorders occur as a result of accidents, disease states, medical interventions, aging, and exposure to environmental pollutants. Furthermore, it is now evident that such problems can serve as important diagnostic signs of a number of serious diseases and anomalies, such as ones associated with Alzheimer's disease, Parkinson's disease, the ontogeny of the hypothalamus and pituitary, intracranial neoplasms, and temporal lobe epilepsy. In fact, it has been suggested that olfactory examinations be routinely performed in pediatric clinics in order to allow for the early identification of endocrine disorders such as Kallmann's Syndrome.

Although the degree of overall impairment from olfactory loss is often less than that produced by major losses in the other senses, smell disturbances are of considerable significance to persons experiencing them. For example, individuals lacking the ability to smell (anosmics) are subject to the consequences of being unable to detect escaping gas, dangerous fumes, and fires in the home, automobile, and workplace. Also, anosmics frequently complain of loss of enjoyment from eating and drinking and must exhibit extreme caution in their eating habits in order to avoid food poisoning from rancid or spoiled food.

Currently, practical, standardized, and carefully psychophysical measurement procedures have not been applied in the field of clinical olfaction. In attempts to quantify the smell function in humans for purposes of clinical testing, two major problems are present: stimulus control and response measurement. To date, the primary manipulations of the stimulus have changed the concentration and the molecular species. Although the flow rate, volume, and temporal patterning of stimulus pulses can also be altered, such manipulations are rarely undertaken in the clinical situation which requires that sensory measurement be completed within a reasonably short period of time. In attempts to minimize the difficulties in stimulus concentration control, numerous techniques for diluting, quantifying, and presenting odorants have been used.

One method used is to dilute the stimulus in relatively odorless liquids in small bottles or flasks ("sniff bottles"). The advantages to this method are that it is simple and flexible; however, interactions between the diluent and odorant can occur in some cases and thereby influence the empirical outcome. Furthermore, such bottles are cumbersome, easily contaminated, and require periodic cleaning and the addition of fresh stimulus material.

The most accurate stimulus presentation procedure is the air dilution olfactometer, that is, the stimulus is diluted by exposing only a portion of it to an air flow induced by the subject's inhalation. Although this procedure is superior to the sniff bottle technique in that it provides accurate concentrations of stimuli to the naris which is not contaminated by the presence of liquid diluent, its practicality in the clinic is limited. That is, usually only one odorant per olfactometer is available at any one time, and considerable effort must be devoted to cleaning and recalibrating the system if a new compound is to be used.

Paralleling the attempts to quantify the stimulus, numerous techniques have been devised to quantify the responses of humans to odorous stimuli, although the majority have been found wanting with regard to precision, sensitivity, or specificity. Such measures have included the influence of odorants on pupillary dilation, respiration rate, blood flow in the extremities, electrical conductivity of the skin, changes in the electroencephalogram, and psychophysical measures of various sorts. Clinical testing has shown that only the psychophysical methods have proved generally useful in quantifying responses to odorants.

Applicant, in his previously filed U.S. patent applications Ser. Nos. 06/589,173 and 06/856,161, now abandoned, discloses a method for testing a person's olfactory function by using booklets containing pre-selected odorant labels. The person taking the test releases the odorant from each of the labels by scratching the same and answers questions regarding each label. The person's answers are then analyzed in order to diagnose the person's olfactory function. The problem with this method, however, is that it requires assistance from medical personnel to analyze the results.

Thus, a need exists for a test which assess a person's sense of smell which is easy to use and to evaluate by the individual taking the test

SUMMARY OF THE INVENTION

The present invention is designed to overcome the deficiencies of the prior art discussed above. It is an object of the present invention to provide a test which assess a person's sense of smell which is easy to use and to evaluate by the individual taking the test.

It is another object of the present invention to provide a clinically acceptable method for testing the olfactory function of an individual.

In accordance with the illustrative embodiments, demonstrating features and advantages of the present invention, there is provided a test panel placed between and movably secured to a front panel and a rear panel. The front panel has two windows located adjacent to each other. Located adjacent the periphery of the test panel are at least twelve odorant means. Each odorant is embedded in microencapsulated crystals that are concentrated in a label. Below each label is a set of four choices. Each choice has means for indicating that that choice has been selected. When the front panel is placed over the test panel and secured thereto only the first set of choices and label should be aligned with their respective windows. In order to use the test, the person is instructed to scratch the label located above the first set of choices and then to immediately sniff the label. The person is then required to select the item which most closely corresponds with what the person smells and to mark it by darkening the circle located adjacent his or her choice. The person then rotates the test panel so that only a second set of choices and label are visible through the windows. The person repeats the procedure of smelling and marking his or her choice. Once the twelfth label has been smelled and the choice marked, the person rotates the front panel wheel a final time. The correctly marked choices will appear in openings formed on the front panel. The person's test score may then be compared to the applicable standards and an evaluation of the person's olfactory function made.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a front perspective view of the present invention;

FIG. 2 is a front elevational view of the present invention prior to the test being taken;

FIG. 3 is a front elevational view of the present invention once the test has been completed; and FIG. 4 is a perspective view of the test panel of the present invention.

DETAILED DESCRIPTION OF THE PREFERRED EMBODIMENT

Referring now to the drawings in detail wherein like reference numerals have been used throughout the various figures to designate like elements, there is shown in FIG. 1 a smell test device constructed in accordance with the principles of the present invention and designated generally as 10.

The test device of the present invention essentially includes a test panel 12 which may be circular. (See FIG. 4.) The test panel 12 has test indicia located thereon. The test panel 12 is placed between and is rotatably secured to a front panel or cover 14 and a rear panel 16 via rivet or similar securing means 18. The front and rear panels 14 and 16 substantially cover the test panel 12, however, enough of the test panel 12 is visible so that the test panel 12 may be grasped and rotated as will be described in greater detail below. The cover 12 has two windows 20 and 22 located adjacent to each other. The test indicia includes at least twelve odorant means 24a–24l, a set of four choices for each odorant, and means for indicating or recording the choice selected.

Located along the periphery of the test panel 12 are the at least twelve odorant means 24a–24l. (FIG. 4.) Each odorant is embedded in microencapsulated crystals that are concentrated in a label. Below each label is the set of four choices, seen for example as 26, with means such as such as circles 28a–28d for recording the selected choice. When the cover 14 is placed over the test panel 12 and secured thereto only the first set of choices 26 and label 24a should be aligned with their respective windows 22 and 20. (See FIG. 1.) The cover 14 also has a series of openings 30a–30l spaced around the cover 14. These openings 30a–30l are positioned to overly the circles 28 representing all of the correct answers when the test panel is rotated into a final position as will be described in greater detail below. (See FIG. 2.) The test panel 12, front panel 14, and rear panel 16 may be made from paper, paperboard, cardboard, plastic or a similar thin flat material.

In order to use the test 10, the person is instructed to scratch the label 24a located above the first set of choices 26 and then to immediately sniff the label 24a. The person is then required to select the item of the set of choices 26 which most closely corresponds with what the he or she smells and to mark it by darkening the circle 28a, 28b, 28c, or 28d located adjacent his or her choice. The person then rotates the test panel 12 so that a second set of choices and label are visible through the windows. The person repeats the procedure of smelling and marking his or her choice.

Once the last or twelfth label has been smelled and the choice marked, the person rotates the test panel 12 a final time. The phrase "Now check your answers" or similar language will appear in the window 22. (See FIG. 3.) The correctly marked choices will appear in the openings 30a–30l formed on the cover 14 as only one of each of the choices accurately describes its respective odorant. (See FIG. 3.) The person's test score may then be compared to the applicable standards and an evaluation of the person's olfactory function made.

The present invention may be embodied in other specific forms without departing from the spirit or essential attributes thereof and accordingly, reference should be made to the appended claims rather than to the foregoing specification as indicating the scope of the invention.

I claim:

1. A test device for assessing a person's olfactory function comprising:

a front panel;

a rear panel;

a test panel having test indicia located thereon, said test indica including at least twelve odorants and a set of choices for each of said odorants from which the person must select the choice which most closely describes each odorant; and means for rotatably securing said test panel between said front and rear panels.

2. The test device for assessing a person's olfactory function of claim 1 wherein said odorants are microencapsulated crystals.

3. The test device for assessing a person's olfactory function of claim 1 wherein only one of said choices in each set of choices describes its respective odorant.

4. The test device for assessing a person's olfactory function of claim 1 wherein said securing means is comprised of a rivet.

* * * * *